United States Patent
Arnow

(10) Patent No.: US 10,251,542 B1
(45) Date of Patent: Apr. 9, 2019

(54) HAND HELD OR EYEGLASS CLIP ON DARK ADAPTION TESTER

(71) Applicant: Daniel Joseph Arnow, New Rochelle, NY (US)

(72) Inventor: Daniel Joseph Arnow, New Rochelle, NY (US)

( * ) Notice: Subject to any disclaimer, the term of this patent is extended or adjusted under 35 U.S.C. 154(b) by 0 days.

(21) Appl. No.: 15/624,461

(22) Filed: Nov. 27, 2017

(51) Int. Cl.
| | |
|---|---|
| *A61B 3/02* | (2006.01) |
| *A61B 3/04* | (2006.01) |
| *A61B 3/06* | (2006.01) |
| *A61B 3/18* | (2006.01) |
| *G02C 9/04* | (2006.01) |

(52) U.S. Cl.
CPC ............... *A61B 3/02* (2013.01); *A61B 3/04* (2013.01); *A61B 3/063* (2013.01); *A61B 3/18* (2013.01); *G02C 9/04* (2013.01)

(58) Field of Classification Search
CPC .. A61B 3/04; A61B 3/063; A61B 3/02; A61B 3/028; A61B 3/066; A61B 3/18; G02C 9/04; G02C 7/10; G02C 7/104
USPC .............................................. 351/47, 44, 57
See application file for complete search history.

(56) References Cited

U.S. PATENT DOCUMENTS

| | | | | |
|---|---|---|---|---|
| 4,783,162 A | * | 11/1988 | Siwoff | G02C 7/10 351/230 |
| 5,208,615 A | * | 5/1993 | Solman | A61B 3/06 351/44 |
| 7,290,878 B1 | * | 11/2007 | Hofeldt | A61B 3/08 351/200 |
| 7,614,746 B2 | | 11/2009 | Severns | |
| 2013/0100400 A1 | * | 4/2013 | Hofeldt | A61B 3/08 351/201 |
| 2017/0255028 A1 | * | 9/2017 | Maggi | G02C 7/105 |
| 2018/0098694 A1 | * | 4/2018 | Schmeder | A61B 3/066 |

* cited by examiner

*Primary Examiner* — Jordan M Schwartz

(57) ABSTRACT

This device consists of a frame and light filters so as to enable a highly portable device to measure Dark Adaption. Dark Adaption is a process which tests sight in low light conditions and is an indicator of wet AMD disease, the leading cause of blindness in older people. This testing process was first established by the Goldmann-Weekers machine in the 1950s. The portability is achieved by use of filters, a common means to light reduction, and elimination of a machine outer cover. The simplicity and portability of this invention allows many types of very substantial cost efficiencies in eye examinations and also greater flexibility. With this device, testing for incipient wet AMD may be achieved in routine eye examinations where it is not now common. Home testing for wet AMD is also made possible and practical with this device.

2 Claims, 1 Drawing Sheet

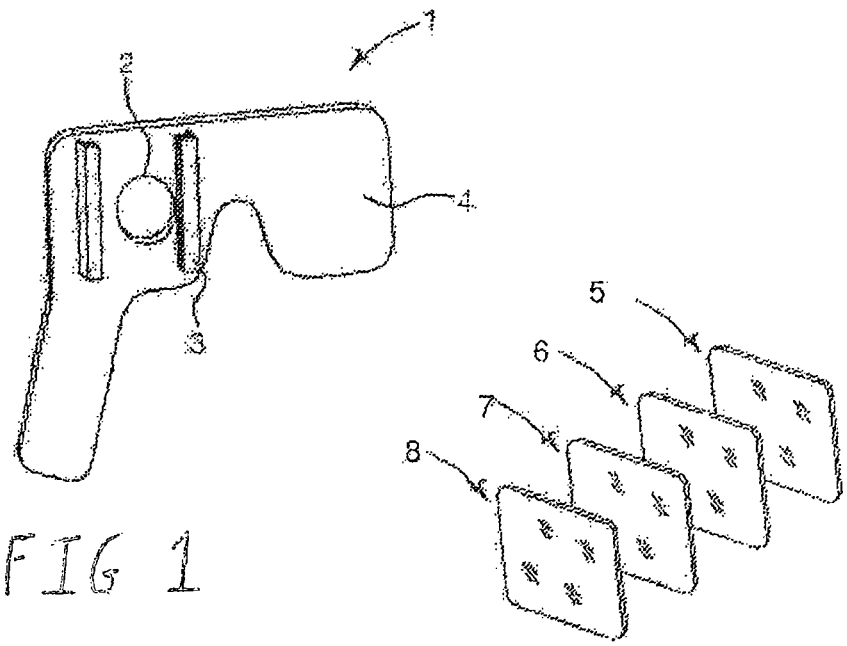
FIG 1
FIG 2
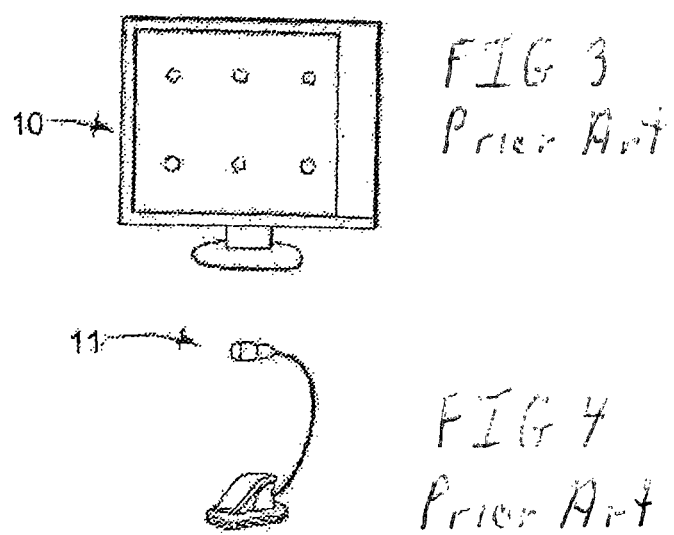
FIG 3
Prior Art
FIG 4
Prior Art

HAND HELD OR EYEGLASS CLIP ON DARK ADAPTION TESTER

The format of this invention is a hand-held occluder similar to those used by Ophthalmologist to which a slide rack has been attached to the right and left of the eye opening in the occluder. The slide rack holds darkening filters of strength number 2 and number 4 and number 8.

To use the above devices, the patient would first take the regular Snellen Eye test with the brightly lighted screen in the doctors office or a brightly light Snellen chart used at home. After the readings are taken OD and OS at regular lighting, the patient may be asked to bleach his vision with a particularly strong light according to the standards of the current art in the field or the brightness of the Snellen chart may prove to have been sufficient. The patient will be asked to rest for a few minutes and then the acuity tests will be repeated OD and OS with the filters covering one eye at a time. New acuity readings will be thus available. If one of the readings is significantly worse in dim light than the full light reading for the same eye, it will be suggestive of dark adaption damage and possible wet AMD implication.

Alternatively or in addition as confirmation the second testing may be done with the patient viewing a small light of fixed known intensity clipped atop the acuity chart machine. The patient would be asked to look for the light as filters of intensity #2, 4, 8 etc. were inserted in the hand held frame until the patient no longer saw the light. difference in readings between OD and OS would be suggestive of loss of Dark Adaption Function in the weaker eye and possibility of AMD.

BACKGROUND OF THE INVENTION

Some prior inventions related to Dark Adaption embellishment to the Goldmann-Weekers machine as selected by a USPTO examiner are:
U.S. Pat. No. 2,247,653 January 1938 Feldman
U.S. Pat. No. 4,545,658 October 1985 Weiss
U.S. Pat. No. 5,080,478 January 1992 O'Brien
U.S. Pat. No. 9,572,485 February 2015 Jackson Dark Adaption is the physical process whereby people lose full ability to see when going from a bright light situation to a dim light situation. People with Macular degeneration disease have weakened dark adaption function. The background of use of dark adaption to recognize macular degeneration disease largely began with the Goldmann-Weekers Dark Adaptometer machine developed about 1950. It dominates the history of this art and was in practical use until very recently but is now no longer manufactured. A series of other machines, based on the Goldmann-Weekers, were developed with various design features claimed to improve performance. These are represented in the list of inventions shown above. In order of the list the improvements included measuring the time for reappearance of a target object (Weiss), automation of the timing of the steps of the Goldmann machine (O'Brien) and use of sophisticated time sequence charts and of the "rod-cone intercept point" as a target factor on the y axis (Jackson).

All of these machines are fairly large and cumbersome although they can be moved as from one room to another or even to be placed in front of the patient but they are usually used from a fixed location. Even if designed for lightness, none would likely to be under 20 pounds as the target object and eye bleaching and other things are included within the machine. The only currently manufactured Dark Adaption machine weighs 46 pounds and measures 17×23×22. The traditional art of light dimming calls for reduction of current to the electric bulb or light source such as by a rheostat or by a light filter between the light source and the viewing eye as in sunglasses.

DESCRIPTION OF COMPONENTS OF THE DRAWINGS

1. An ocular assembly with cutouts for one eye and the nose and one eye's view occluded such that the patient can view the acuity charts or light source through a single eye across an open field of visual communication between the patient and the visual objectives.
2. The eyehole of the occluder assembly through which the patient will view the objectives at the other end of the longitudinal field of visual communication.
3. The slider rack to hold neutral density darkness filters.
4. The occluded portion of eyepiece.
5. Number 2 darkness filter reducing light to one half intensity. The darkness filters are used to establish the threshold of blindness of the patient under varying conditions.
6. Number 4 darkness filter reducing light to one quarter intensity.
7. Number 8 darkness filter reducing light to one eighth intensity.
8. A filter of undetermined type to represent the ability to add new filters.
9. An Acuity Chart as the type two objective described in the procedure section of the Detailed Description. It is an electrically lighted chart as commonly used in Ophthalmologists offices.
10. A clip-on constant intensity light source as the type used in the prior art

BRIEF SUMMARY OF THE INVENTION

The invention herein envisioned would allow inexpensive and easy screening for wet AMD in routine ophthalmological examinations and in home situations. Such special screening for wet AMD is not being done at the current time. This special screening would allow many more cases of incipient wet AMD to be caught early. As in the case of cancer, early detection is the key to successful treatment of wet AMD. The above benefits would be achieved by the lightness and portability of this hand held tester which would allow quick and easy testing immediately after the standard acuity test introducing only the small light filters attached to the viewer bases.

BRIEF DESCRIPTION OF THE DRAWINGS

FIG. 1 is the optical occluder with the slotted rack.
FIG. 2 are the number 2, number 4, number 8 and any additional filter(s) that can be placed in the slotted rack of the invention.
FIG. 3 is an Acuity Chart as the type two objective described in the procedure section of the Detailed Description. It is an electrically lighted chart as commonly used in Ophthalmologist's offices.
FIG. 4 is a clip-on constant intensity light source as the type used in the prior art.

DETAILED DESCRIPTION OF THE INVENTION

This product is intended to fill the need for a broadly used screening device to catch wet AMD early when it is most treatable. Existing devices all have some issue which is practically preventing their use in routine examinations. The Amsler grid test has been found to allow too many false positives. Existing Dark Adaption testing devices derived from the original Goldmann-Weekers machine originating in about 1950 have a in-use cost above that direct diagram examination of CNV blood accumulation with an OCT exam as indicated below and so are not favored by Ophthalmologists. And even the cost of the direct diagram analysis with an OCT exam is considered too high for routine clinical eye examinations. As a result, no broad scale screening of general eye care patients for wet AMD is being done currently. It is anticipated that this product will cut the cost of dark adaption testing by three quarters so that insurance companies may accept it's use on all routine eye examinations. It is expected that it will be as easily done as an eye pressure test for Glaucoma screening or an acuity test. In fact, in the most basic form this test will be no more complicated than doing an acuity test a second time. It is this simplification and operating cost reduction and "manufacturing" process improvement which is the heart of this invention.

The invention is presented as an optical occluder with a slotted "rack" attached to the occluder on each side of the eye hole. The other eye is blocked by the opaque side of ocular assembly.

The object of the invention is to measure the dark adaption factor of the eye. AMD rarely strikes both eyes simultaneously so a marked difference in dark adaption between the two eyes is suggestive of a weak dark adaption and wet AMD disease.

The basic dark accommodation scientific factor is that an eye affected by wet AMD will show weakened ability to see when the light goes from bright to dim. This scientific function was originally developed with the Goldmann-Weekers machine mentioned in the background section. The invention herein presents this situation to the patient with bright light followed by dimmer light created by light filters covering the eye to be tested.

Traditionally, there have always been two practical methods to reduce the lighting - - - by reducing the electricity to the light source and by filtering the light as viewed by the observer. This invention uses the less common latter method.

The procedure of the test would be as follows: The patient takes a standard acuity test. Then a bleaching light may be shown to the patient as needed if insufficient bleaching was not accomplished by the lighting. A few minutes later, the patient is asked to view the same acuity chart a second time through the light filter, which imposes a neutral density filter between the patient's eye and the same acuity chart previously viewed. This is done for both eyes. If the patient has incipient wet AMD in one eye, that eye will show a marked decline in the acuity reading the patient is able to read.

Alternatively, similar testing may be done with a constant intensity light source sitting on top of the acuity chart instead of the acuity chart itself. Patient will be tested with different filters to see the minimum darkness filter needed to just see the light before and after being exposed to a bright light. This testing with a constant light source will be more reflective of the dark adaption of rod cells to a light source whereas the testing with the acuity chart will be more reflective of reduced acuity performance of cone cells in a dim light situation.

Since the target viewed objective is also outside the machine, the above two methods may be used alternatively, allowing unique machine flexibility.

Removing the machine cover leads to ergonomic, economic, and flexibility and weight advantages which will be claimed as constituting the inventive character of this machine.

With regard to patent infringement, it is important to note that the device herein uses none of the claimed improvements on the basic Goldmann Weekers machine of 1950. The later patents listed in the background section above deal mostly with improved recorded patterns of vision loss over time including mathematical treatments of results. But none of these "improvements" after the 1950 Goldman machine is utilized by the invention herein. The Goldmann machine is not usually given credit in the patent applications of the later inventions in the art perhaps because of it's foreign source and time lapse. But the Goldmann machine is widely recognized in medical literature and clinical procedures as the source of dark adaption testing. In it's basic form, the device herein takes a one-time, static reading of vision loss similar to that as performed by the Goldmann machine from 1950.

Because it is a light and simple, the device is expected to have an initial cost and use costs only a fraction of the large-box machines. Testing may be done at home as well as in the doctor's office. The time required to do the testing is reduced to less than a few minutes with a short break to allow for the dark adaption process. No highly trained technicians are required. The staff person who gives the acuity test can do it easily in the same chair. And no complex interpretations of highly scientific charts by the doctor are required.

With regard to cost usage costs as measured by the costs of related Medicare Procedure Codes, it is important to note that the cost point of this product will be well below that of an OCT-Macula test which is the current diagnostic standard for wet AMD. The OCT-Macula is a diagnostic imaging procedure that corresponds to an X-ray type picture of the underlying CNV disease. Meanwhile, the costs of the existing dark adaption devices on the market are well above that of an OCT-Macula and believed to be more than double the cost to insurer. For this economic reason, the existing dark adaption measuring devices suffer in comparison to the choice of an OCT-Macula. Moreover, both the OCT-Macula test and traditional dark adaption testing are both currently considered too "expensive" to be used in routine optical examinations. As of 2016, the Medicare approved cost to the insurer of Diagnostic Retina Imaging (OCT-Macula) was $32.50. Medicare cost of a full dye angiogram, considered the gold standard of AMD diagnosis, is about $82. Meanwhile, Medicare cost of an examination with the only currently manufactured Dark Adaption Tester has been estimated at about $62.

This dark adaption test herein may be given in conjunction with other effective tests. For example, the quick and efficient Amsler Grid Test is highly effective in diagnosing wet AMD, but has not been used in most routine Ophthalmological examinations because of claimed excessive instances of false positives. Testing with this device combined with the Amsler test would be highly reliable and cost effective. Positive initial results with this machine could also be further verified with the larger dark adaption machines or OCT or angiogram as determined by the doctor.

With regard to the advantages of being able to be held in the hand, inventor herein declares that this ability not just a matter of size. An ancient example even appears in the Bible where it is directed that if the way be too far or the load be to heavy to carry the goods to Jerusalem for a festival day, the goods should be turned to money and the money carried in the hand to the city and there converted back to goods for the festival; Deuteronomy 14:24 &25

Many of the other patent applications mentioned above in the prior art discussion in the background section have discussed wet AMD statistics world-wide where millions of people are blinded who might be saved with early detection. The applicant would wish to incorporate their discussions here. The current target population of patients with wet AMD is estimated at 1.1 million in the US alone and about 20 to 25 million world wide assuming even distribution of the disease Some of the new features offered by this device relate to greatly reduced cost. Many of the world's most important inventions such as the Bessemer Steel Process have been due to significant reductions in the costs of the process rather than entirely new goods. The benefits presented by the apparatus structure herein include:

1. Hand-carry convenience allowing the machine to be brought to the patient instead of vice versa.

2. Flexible use of an objective of either an acuity chart or a light source allows dark adaptation measurements to be made relative to cone or rods cells independently.

3. Cost point in Medicare Procedure Codes below that of retina imaging (OCT) allowing approval by insurers and wide scale preventive care use.

4. Flexibility to be easily used with other simple tests such as the Amsler test and still maintain a low cost point.

5. Simplicity of testing requiring little time or technician expertise.

6. Ability to be used in primitive situations without electricity.

7. Elimination of heavy and cumbersome and useless machine casing. The apparatus herein is not delicate, has no moving parts and is not subject to damage or adjustment

The invention claimed is:

1. An ocular assembly for testing a patient for age-related macular degeneration, the ocular assembly comprising the following:

A thin, lightweight hand held assembly having a handle, a nose cut-out portion: the nose cut-out portion sized and shaped to cover the nose of a user when in use, the hand held assembly having a first portion constructed to be positioned over the first eye of the patient and a second portion constructed to be positioned over a second eye of the patient, the first portion of the hand held assembly being constructed as a light occluding portion to totally block the first eye from seeing an object, the second portion of the hand held assembly having an opening and further having first and second slotted portions, the first and second slotted portions being positioned on opposite sides of the opening, the first and second slotted portions sized and shaped to permit different neutral density filters to be inserted and removed from the slotted portions to thereby be positioned in front of the opening, the hand held assembly being constructed such that when the patient holds the handle and positions the nose cut-out portion over the nose of the patient with a neutral density filter inserted into the slotted portions, the first portion of the hand held assembly completely blocks the first eye from seeing an object and the second portion of the hand held assembly permits the patient to view the object through the neutral density filter that is inserted into the slotted portions;

the ocular assembly further comprising a first neutral density filter being a number 2 filter that provides one-half light transmission, the first neutral density filter being sized and shaped to fit into the first and second slotted portions of the hand held assembly such that the first neutral density filter can be inserted and removed from the first and second slotted portions, the ocular assembly further comprising a second neutral density filter being a number 4 filter that provides one-quarter light transmission, the second neutral density filter being sized and shaped to fit into the first and second slotted portions of the hand held assembly such that the second neutral density filter can be inserted and removed from the first and second slotted portions, the ocular assembly further comprising a third neutral density filter being a number 8 filter that provides one-eighth light transmission, the third neutral density filter being sized and shaped to fit into the first and second slotted portions of the hand held assembly such that the third neutral density filter can be inserted and removed from the first and second slotted portions.

2. A method for testing a patient for age-related macular degeneration comprising the following steps:

providing a thin, lightweight hand held assembly having a handle, a nose cut-out portion, the nose cut-out portion sized and shaped to cover tile nose of a user when in use, the hand held assembly having a first portion constructed to be positioned over the first eye of the patient and a second portion constructed to be positioned over a second eye of the patient, the first portion of the hand held assembly being constructed as a light occluding portion to totally block the first eye from seeing an object, the second portion of the hand held assembly having an opening and further having first and second slotted portions: the first and second slotted portions being positioned on opposite sides of the opening, the first and second slotted portions sized and shaped to permit different neutral density filters to be inserted and removed from the slotted portions to thereby be positioned in front of the opening: the hand held assembly being constructed such that when the patient holds the handle and positions the nose cut-out portion over the nose of the patient with a neutral density filter inserted into the slotted portions, the first portion of the hand held assembly completely blocks the first eye from seeing an object and the second portion of the hand held assembly permits the patient to view the object through the neutral density filter that is inserted into the slotted portions;

inserting into the slotted portions of the hand held assembly a first neutral density filter being a number 2 filter that provides one-half light transmission, the first neutral density filter being sized and shaped to fit into the first and second slotted portions of the hand held assembly such that the first neutral density filter can be inserted and removed from the first and second slotted portions;

having the patient hold the handle and position the hand held assembly in front of the eyes of the patient with the nose of the patient inserted into the nose cut-out portion, the hand held assembly positioned such that the first portion of the hand held assembly is positioned in front of the first eye of the patient thereby occluding the light to the first eye and the second portion of the hand held assembly is positioned in front of the second eye of the patient thereby allowing the patient to view the object through the first filter;

testing the second eye of the patient as the patient views the object to determine if the patient has dark adaption damage while viewing the object through the first filter;

inserting into the slotted portions of the hand held assembly a second neutral density filter being a number 4 filter that provides one-quarter light transmission, the second neutral density filter being sized and shaped to fit into the first and second slotted portions of the hand held assembly such that the second neutral density filter can be inserted and removed from the first and second slotted portions;

having the patient hold the handle and position the hand held assembly in front of the eyes of the patient with the nose of the patient inserted into the nose cut-out portion, the hand held assembly positioned such that the first portion of the hand held assembly is positioned in front of the first eye of the patient thereby occluding the light to the first eye and the second portion of the hand held assembly is positioned in front of the second eye of the patient thereby allowing the patient to view the object through the second filter testing the second eye of the patient as the patient views the object to determine if the patient has dark adaption damage while viewing the object through the second fitter;

inserting into the slotted portions of the hand held assembly a third neutral density filter being a number 8 filter that provides one-eighth light transmission, the third neutral density filter being sized and shaped to fit into the first and second slotted portions of the hand held assembly such that the third neutral density filter can be inserted and removed from the first and second slotted portions;

having the patient hold the handle and position the hand held assembly in front of the eyes of the patient with the nose of the patient inserted into the nose cut-out portion, the hand held assembly positioned such that the first portion of the hand held assembly is positioned in front of the first eye of the patient thereby occluding the light to the first eye and the second portion of the hand held assembly is positioned in front of the second eye of the patient thereby allowing the patient to view the object through the third filter;

testing the second eye of the patient as the patient views the object to determine if the patient has dark adaption damage while viewing the object through the third filter;

determining from the patient's viewing of the object through the number 2, number 4 and number 8 filters if the patient has dark adaption damage in the second eye to test the patient in determining if the patient has age related macular degeneration in the second eye.

* * * * *